United States Patent [19]
Svetkoff et al.

[11] Patent Number: 6,028,671
[45] Date of Patent: *Feb. 22, 2000

[54] METHOD AND SYSTEM FOR SUPPRESSING UNWANTED REFLECTIONS IN AN OPTICAL SYSTEM

[75] Inventors: Donald J. Svetkoff, Ann Arbor; Donald B. T. Kilgus, Brighton, both of Mich.

[73] Assignee: General Scanning, Inc., Simi Valley, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/594,696

[22] Filed: Jan. 31, 1996

[51] Int. Cl.$^7$ ........................................... G01J 4/00
[52] U.S. Cl. ............................................. 356/368
[58] Field of Search ................... 356/368, 369; 250/225

[56] References Cited

U.S. PATENT DOCUMENTS 3,443,072  5/1969  Mori.
3,502,888  3/1970  Stites.

(List continued on next page.)

FOREIGN PATENT DOCUMENTS 9409463  4/1994  WIPO.

OTHER PUBLICATIONS

Polarization–based Peak Detection in Laser Triangulation Range Sensors, J. Clark & E. Trucco, Dept. of Computing and Electrical Engineering, Heriot–Warr University, Edinburgh, Jan., 1996.

Improving Laser Triangulation Sensors Using Polarization, J. Clark, E. Trucco, H.F. Cheung, Department of Computing and Electrical Engineering, Heriot–Watt University, Edinburgh, Scotland, Aug. 1995.

Computer Vision Systems, "Recovering Intrinsic Scene Characteristics from Images", Computer and Information Science Department, University of Massachusetts, Amherst, Masssachusetts, Jun. 1977, pp. 3–26.

The Infrared Handbook, Office of Naval Research, Department of Navy, 1978, pp. 19–22 and 19–23.

Understanding Image Intensities, Artificial Intelligence, pp. 201–231. Aug. 1977.

Fundamentals of Optics, 4th Edition 1996 pp. 534–540.

*Primary Examiner*—K. P. Hantis
*Attorney, Agent, or Firm*—Brooks & Kushman P.C.

[57] ABSTRACT

A method and system are provided for suppressing or filtering multiple reflections which corrupt photometric (grey scale or color) or height measurements within optical systems such as imaging systems. The reflections may originate within the instrument (i.e. back reflections) or may be inter-reflections between one or more surfaces in a scene. In one embodiment, a beam of electromagnetic energy generated by a source is polarized in a first rotational sense, is transmitted to a point of interest (i.e., scene) of an object, is reflected and received by a receiver having a polarizer which passes reflected electromagnetic energy having a second rotational sense opposite the first rotational sense. In this way, unwanted reflections from the point of interest having the first rotational sense are suppressed and back-reflections to the source of electromagnetic energy are substantially eliminated. In another embodiment, a detector which normally back-reflects a portion of electromagnetic energy it receives along a first axis, has a surface normal which is maintained in a fixed, non-colinear relation to the first axis and back-reflected electromagnetic energy is prevented from reaching the scene and, consequently, is not received by any other detector of the imaging system. The method and system are particularly well suited for use in 3D imaging systems and measurement systems utilizing a beam of electromagnetic energy and multiple detectors.

2 Claims, 10 Drawing Sheets

U.S. PATENT DOCUMENTS

| | | |
|---|---|---|
| 4,339,660 | 7/1982 | Buchholz et al. . |
| 4,529,316 | 7/1985 | DiMatteo . |
| 4,553,844 | 11/1985 | Nakagawa et al. . |
| 4,634,879 | 1/1987 | Penney . |
| 4,643,578 | 2/1987 | Stern . |
| 4,645,917 | 2/1987 | Penney et al. . |
| 4,796,997 | 1/1989 | Svetkoff et al. . |
| 4,891,772 | 1/1990 | Case et al. . |
| 4,967,152 | 10/1990 | Patterson . |
| 5,024,529 | 6/1991 | Svetkoff et al. . |
| 5,028,138 | 7/1991 | Wolff . |
| 5,118,191 | 6/1992 | Hopkins . |
| 5,118,192 | 6/1992 | Chen et al. . |
| 5,850,284 | 12/1998 | Schoeffler et al. . |

METHOD AND SYSTEM FOR SUPPRESSING UNWANTED REFLECTIONS IN AN OPTICAL SYSTEM

CROSS-REFERENCE TO RELATED APPLICATIONS

This application is related to U.S. patent application Ser. No. 08/245,864 entitled "Triangulation-Based 3D Imaging and Processing Method and System," filed May 19, 1994, and U.S. patent application Ser. No. 08/429,543 entitled "Method and System for Triangulation-Based, 3-D Imaging Utilizing an Angled Scanning Beam of Radiant Energy," filed Apr. 27, 1995, both of which are hereby incorporated in their entirety by reference herein.

TECHNICAL FIELD

This invention relates to methods and systems for suppressing or filtering unwanted reflections in an optical system.

BACKGROUND ART

Over the past several years the benefits of 3D imaging for metrology and inspection has been recognized. Applications of 3D imaging range from microelectronics inspection to mobile robot navigation, with data rates from a few hundred points per second to video rates. Accuracy of these systems is limited, at the most fundamental level, by the underlying physics of the imaging process.

Illumination Distribution and Imaging Errors

In all 3D systems the distribution of incident illumination upon a detector is analyzed in some manner, and the corresponding temporal or spatial variations analyzed to estimate the object reflectance and/or depth. Usually, the centroid of the intensity distribution is analyzed to determine the position of a point on the object surface. As such, position dependent anomalies which corrupt the intensity distribution lead to inaccuracies which may vary from a negligible "noise" contribution to visible artifacts producing very large errors which may render the imaging system useless.

Early researchers in computer vision recognized the importance of the physics of imaging and the image formation process for scene modeling and understanding. For instance, Horn in his article entitled "Understanding Image Intensities," Artificial Intelligence (1977) pp. 201–231, considered numerous imaging phenomena, including the effect of "mutual illumination," when investigating the relationship between observed image intensity and surface characteristics and geometry.

Barrow and Tennenbaum, in their article entitled "Recovering Intrinsic Scene Characteristics from Images," Computer Vision Systems (1978) pp. 3–26, developed a model of "Intrinsic Images," which related an array of intensity values and physical surface properties like depth, reflectance, and surface orientation. They were cautious, however, to limit their model based upon assumptions about the illumination, including a limitation requiring that no secondary reflections be present. Violation of this assumption would render the model invalid because of the ambiguous interpretation of a single image.

3D Imaging and Errors Caused by Inter-Reflections

Many real-world imaging applications involve estimation of more complex geometries. Objects having such geometries and, in particular, concave shapes are susceptible to the occurrence of multiple reflections within the instantaneous field of view ("IFOV"), thus leading to ambiguous image data. The reflections of the energy by the surface which allow the imaging to take place may be either specular (direct), diffuse (scattered), or, usually, components of both. The multiplicity of image points falling on the sensor can make it impossible to determine the correct height estimate, as only one point represents the true object point of interest. The ambiguity generally leads either to an uncertain choice as to which is the correct image point or a weighted average of the various image points which lead to an incorrect estimate.

A large percentage of 3D imaging techniques now in use are based upon the triangulation principle. Several references discuss the limitations of instruments based upon triangulation, the most well known limitation being occlusion effects.

However, there are fewer studies discussing the less obvious, but perhaps even more severe, limitation associated with secondary reflections (also called intra-scene reflections, inter-reflections, mutual illumination, secondary illumination, multiple reflections, self illumination, multiple scatterings, etc.). The problem originates from energy received by a detector which is reflected from the object point of interest to other regions of the scene prior to being received by the detector.

The problem is inherent in all triangulation based systems because the necessary extended IFOV along the position sensing axis allows for integration of secondary reflections. It is not uncommon for the secondary reflected beam to contain a strong specular component exceeding the signal obtained from the point of interest, thereby invalidating a typical naive assumption that the largest intensity reading corresponds to the point of interest.

It is important to note that the 3D imaging problem, particularly for triangulation based imaging, can become very complex when imaging curved, specular surfaces which also produce partial occlusion. As taught by Barrow and Tennenbaum noted above, the stray light associated with the occluded regions can be stronger or competitive with primary returns from other points of interest.

Steep slopes and small radii of curvature which are on the order of the system resolution lead to extreme requirements for electronic and optical dynamic range. Perhaps a worst case scenario to consider is thread gaging of a shiny, fine pitch screw with viewpoint of the triangulation receiver constrained as shown in FIG. 1. Such a scenario requires very wide electronic and optical dynamic range.

Prior Art Solutions for Reducing Imaging Errors

Intra-Scene Reflections

Spatial filtering methods taught in the art have been reasonably successful for reduction of secondary reflection components along the scan direction (i.e. substantially orthogonal to the position sensing dimension).

U.S. Pat. No. 4,553,844 (Nakagawa et al.) describes filtering of strong multiple reflections which corrupt 3D data for measurement of solder joints. The IFOV along the scan direction is limited to a narrow strip within an object scanned system in which a "descanning" method is used. There is no discussion, however, about suppression of errors along a position sensing axis.

U.S. Pat. No. 4,643,578 (Stern) teaches the use of a programmable mask in a detector plane synchronized with motion of a laser spot to reject strong background energy. Unwanted energy resulted from welding are glare and ambient light. This method allows for synchronization with standard t.v. sensors and eliminates moving parts.

U.S. Pat. No. 4,634,879 (Penney) and U.S. Pat. No. 4,645,917 (Penney et al.) describe the use of a small mask to reject background light in a similar laser scanning/descanning system, performing a similar function.

"Synchronous scanning" techniques as described in these references have inherent spatial filtering capability.

However, the required IFOV substantially along the position sensing direction often allows for much stronger secondary reflection components to be received, particularly for systems having extended depth of field requirements where surfaces are located in close proximity. In restricted application scenarios, like microelectronics inspection, reduction in this error can be achieved with appropriate adjustments of the viewpoint and the use of multiple sources and detectors and knowledge based data processing techniques. Examples are shown in the above co-pending applications, U.S. Pat. No. 4,529,316 (DiMatteo), U.S. Pat. No. 5,118,192 (Chen et al.), U.S. Pat. No. 4,891,772 (Case et al.) and a commercial IPK system manufactured by Panasonic Inc.

In U.S. Pat. Nos. 5,024,529 and 4,796,997 (Svetkoff et al.), the use of a mask, preferably one which is programmable, is taught in which the IFOV along the height (position sensing dimension) is correlated with the height profile of the object to be inspected. If the mask is used with appropriate polarizers, the polarization delivered to the detector can be selected. Inherent in the laser scanning (transmitter) system is a beam of linear or circular polarized light incident upon the object (produced by the combination of a laser and AO deflector). The use of polarization discrimination in conjunction with the mask was suggested in the '529 patent for eliminating errors associated with shiny objects like metallic interconnects in electronics industry: wire bonds, pin grid arrays, reflowed solder, etc.

Another method to suppress or filter multiple reflections is to orient the projection and imaging subsystems so as to be symmetric about the normal to the surfaces to be imaged and utilize matched linear polarizers in the two subsystems. In this method only specular reflections are deemed to be of interest. Secondary and tertiary reflections which remain within the IFOV are of necessity; the product of at least one diffuse reflection. Since diffuse reflections are known to partially de-polarize incident light, these reflections are suppressed by the linear polarizer in the second subsystem. This technique is not useful for objects which have complex, sharply varying, or concave surfaces, however, as the symmetric orientation condition will generally not be met unless the orientation of the projector and the receiver are adjusted.

In U.S. Pat. No. 5,028,138 (Wolff), a polarization-based method for material classification is disclosed in which specular and diffuse components resulting from multiple reflections can be distinguished. The method is based upon a receiver oriented to receive specular reflected light. A multiplicity of received polarization components are analyzed.

PCT published application WO 94/09463 discloses an apparatus for detecting ice or snow on a surface including a linear polarizer and a wave retarder plate which charges linearly polarized light into circularly polarized light.

Recent polarization-based research work disclosed by Clark et. al. in their articles entitled "Polarization Based Peak Detection in Triangulation Range Sensors" and "Improving Laser Triangulation Sensors Using Polarization," 0-8186-7042-8/95 IEEE also demonstrates specific improvements in triangulation based imagery with the use of polarization discrimination as suggested in the aforementioned earlier work. A LCD camera is preferred to analyze three polarization component images (typically with 0°, 45°, and 90° analyzer orientations) to reduce or eliminate the ambiguity associated with the important case of metal—metal inter-reflections. The cited work in progress will be extended to dielectric and translucent surfaces.

Instrument-Based Back-Reflections

Yet another problem can arise to further corrupt the measurements. Back reflection from the instrument onto the scene can modify the intensity distribution, particularly when multiple detectors are used (which are intended for the purpose of reducing reflection artifacts in addition to eliminating occlusion). It is known in the illumination and spectral measurement art that wedged windows are useful for eliminating second surface reflections which normally occur with parallel windows, and such reflections corrupt spectral measurements. An increase in the wedge angle provides for increased reflected beam angular separation at a distance. Although not widely documented, in commercial fiber optic systems, back-reflection introduces non-uniformity in the delivered illumination and thermal effects at the source which is sometimes reduced by tilting the light source with respect to the fiber by several degrees.

"Self imaging" effects called "narcissism" are considered in imaging system design (i.e., see, for example, W. L. Wolfe, "Imaging Systems," Infrared Handbook Infrared Information and Analysis Center, 1978, Chapter 19, pp. 19–22,19–23). A single detector views a constant field and stray radiation is negligible. The back reflection problem just described is different in that 1) a second detector receives a weak component of reflected light from the point of interest; 2) the object is sequentially illuminated; and 3) the second detector receives a significant component of stray reflected energy. In the reference cited immediately above, it is noted that spurious reflections can cause crosstalk with neighboring elements of a detector array, the reflections originating from other surfaces within the optical system.

Back-Reflection Effects on Laser Beam

Furthermore, systems utilizing lasers for scanning a beam or projecting a line can be degraded by "feedback light." Specular (or semi-specular) back reflection from the scene may induce destructive interference in the laser and induce improper laser operation. In effect, the scene, in combination with optical surfaces, acts like an external cavity mirror. In prior art systems, optical isolators were used to eliminate this undesirable phenomena.

SUMMARY OF THE INVENTION

It is an object of the present invention to provide a method and system which suppress unwanted reflections in optical systems with the addition of little hardware, and with minimal modifications to the optical system. The effects of both scene and instrument-based inter-reflections are eliminated while simultaneously isolating a laser source of the optical system from scene back-reflections. Such a method and system for suppressing inter-reflections is particularly important in a 3D imaging system, or whenever measurement of the intensity distribution is required.

Another object of the invention is to provide a method and system which suppresses unwanted reflections in optical systems which utilize a measure of the intensity or intensity distribution of electromagnetic energy such as incident light. The method and system reduce errors caused by instrument and scene inter-reflections to negligible levels, thereby improving performance of such optical systems.

Yet another object of the present invention is to provide a method and system to suppress unwanted reflections of an optical system by utilizing a transmitted beam of electromagnetic energy polarized in a first rotational sense to eliminate unwanted back reflection into a laser diode cavity, yet provide for reduction of detected object inter-reflections by means of polarization discrimination or selection in a receiver of the optical system.

Yet still another object of the present invention is to provide a method and system to suppress unwanted reflections in an optical system having multiple detectors by reducing errors caused by back reflection from one of the detectors which is then reflected from a surface in the scene and then received by another one of the detectors.

Another object of the present invention is to provide a method and system for suppressing unwanted reflections in an optical system to allow for reduction of triangulation angle (for example, 20° or less) through suppression of strong, secondary reflection components, particularly on metallic surfaces by exploiting known polarization characteristics associated with narrow angles of incidence.

Yet a further object of the present invention is to provide a method and system for suppressing unwanted reflections in an optical system while having a minimal impact on the hardware components and package dimensions of the optical system.

In carrying out the above objects and other objects of the present invention, a method is provided for suppressing unwanted reflections in an optical system. The imaging system includes a source of electromagnetic energy and optical elements for directing a beam of the electromagnetic energy to an object having a point of interest. The object is capable of reflecting the beam of electromagnetic energy to obtain reflected electromagnetic energy. The imaging system also includes a receiver having a detector for collecting the reflected electromagnetic energy. The improvement of the method includes the step of polarizing the beam of electromagnetic energy in a first rotational sense. The polarized beam of electromagnetic energy is incident upon the point of interest of the object. The method further includes the step of filtering the reflected electromagnetic energy wherein reflected electromagnetic energy having the first rotational sense is attenuated and reflected electromagnetic energy having a second rotational sense substantially opposite to the first rotational sense is passed. Consequently, unwanted reflections from locations other than the point of interest on the object are suppressed and back reflections to the source of electromagnetic energy are substantially eliminated.

Further in carrying out the above objects and other objects of the present invention, another method is provided for suppressing unwanted reflections in an optical system including at least one detector having a surface normal. The detector back-reflects a fraction of electromagnetic energy received from a scene to be imaged along a first axis to obtain back-reflected electromagnetic energy. The improvement of the method includes the step of maintaining the detector so that the surface normal of the detector is in a fixed, non-colinear relation to the first axis. The method further includes the step of preventing the back-related electromagnetic energy from reaching the scene. The back-reflected electromagnetic energy is not received by any other detector of the imaging system.

Still further in carrying out the above objects and other objects of the present invention, systems are provided for carrying out the methods of the present invention.

Similar methods involving tilting of a detector are useful in dual sensor 3D systems as shown herein and can be incorporated without special modifications of the detector window, substrate geometry, or metallization properties.

The well documented properties of the circular polarization solution is convenient and very efficient as a single passive optical element rejects the unwanted beam. Hence, it is advantageous to use circular polarization in the transmitter beam when a laser-based system is used.

A well-known aspect of polarization theory is the 180 degree phase shift of a linear polarized component of a electromagnetic wave upon specular reflection from a surface. Also well-known is that circular polarization, being described as arising from the combination of two orthogonal linear polarization components, is reversed in state from right-handed to left-handed or vice versa as a result of a specular reflection. The handedness of the polarization defines which of the two linear components of the circular polarized beam is leading the other in phase by 90 degrees. It follows, then, that multiple reflections will lead to polarization state reversals back and forth between right- and left-handed with odd or even number of reflections.

One useful application of the above described phenomenon is the use of a circular polarizer (often, but not always, a combination of a linear polarizer and a quarter-wave retarder) in the projector subsystem of an active 3D imaging system to suppress direct reflections from the object back into the projector subsystem. Circular polarizers pass waves of a particular handedness of circular polarization while blocking waves of the opposite handedness. For instance, a circular polarizer might be used which, by design, transmits only left-handed circular polarized (LCP) energy. After the state reversal of a direct reflection, the transmitted LCP wave becomes right-handed circular polarized (RCP) and is blocked from re-entry into the projector subsystem.

A first embodiment of the present invention entails utilization of a pair of circular polarizers, of opposite handedness from one another, in the respective beam paths of the projector and imaging subsystems. Thus the projector subsystem might transmit an LCP wave. Since the desired imaging of the points of interest entails a single reflection, we expect an RCP wave to enter the imaging subsystem. Inclusion of an RCP-passing circular-polarizer in the imaging subsystem, then, allows imaging of the points of interest. However, when an object geometry arises such that two reflections occur within the imaging subsystem IFOV, the portion of the wave which undergoes the two reflections will be LCP again and will be blocked by the imaging subsystem circular polarizer.

Thus, when a laser source is utilized, it is isolated from back reflections from the scene while at the same time secondary scene reflections are at least partially suppressed in the receiver subsystem.

A second embodiment of the present invention, which may or may not be used in conjunction with the first embodiment, is to utilize tilted image detectors so that back reflections to the scene from the sensor are angularly deviated from the incoming beams. Since triangulation systems with multiple imaging subsystems and image sensors generally orient the optical axes of such subsystems to be substantially symmetric about the normal to the scene being imaged and to exist in a plane which is perpendicular to the surface, a beam back-reflected from the sensor to the scene will, if not angularly deviated in some manner, reflect in a substantially specular manner from the scene into the oppositely oriented sensor. By utilizing a tilted detector, which may have a substantial reflectance value, the present invention creates a situation whereby any back reflections from the sensor will be substantially extinguished by optical baffles or similar means within the receiver subsystem.

The invention of the first embodiment is an improved imaging method in an imaging system having a beam of electromagnetic energy, optical elements for directing said beam of electromagnetic energy to an object having a point of interest and capable of scattering or reflecting energy, and a receiver system having a detector for collected reflected or scattered energy. The improvement comprises 1) a transmitted beam of circularly polarized electromagnetic radiation having a first rotational sense, incident upon a point of interest on said object; and 2) a receiver having a circular or elliptical polarizer, where the circular or elliptical polarizer rotational sense is oriented substantially opposite to that of the transmitted beam of circularly polarized radiation. Secondary and other even numbered reflections from locations other than point of interest on object are suppressed with the receiver circular polarizer while simultaneously suppressing unwanted back reflections from the scene to the laser source.

The invention of the second embodiment includes an improved imaging method in an imaging system having at least one detector which back-reflects a fraction of received electromagnetic energy to a scene to be imaged. The improvement comprises 1) orienting the detector at an angle so as to separate the angle of reflection of the back-reflected energy from the incident beam; and 2) intercepting the back reflected beam with a surface disjointed from the scene to be imaged. The back-reflection to the scene is substantially eliminated and not received by any detector in the system.

The above objects and other objects, features, and advantages of the present invention are readily apparent from the following detailed description of the best mode for carrying out the invention when taken in connection with the accompanying drawings.

Best Mode For Carrying Out The Invention

While preferred embodiments of the invention are discussed separately herein, the two methods and systems can be used alone or in combination with one another.

Using A Pair of Circular Polarizers

Figure 3:
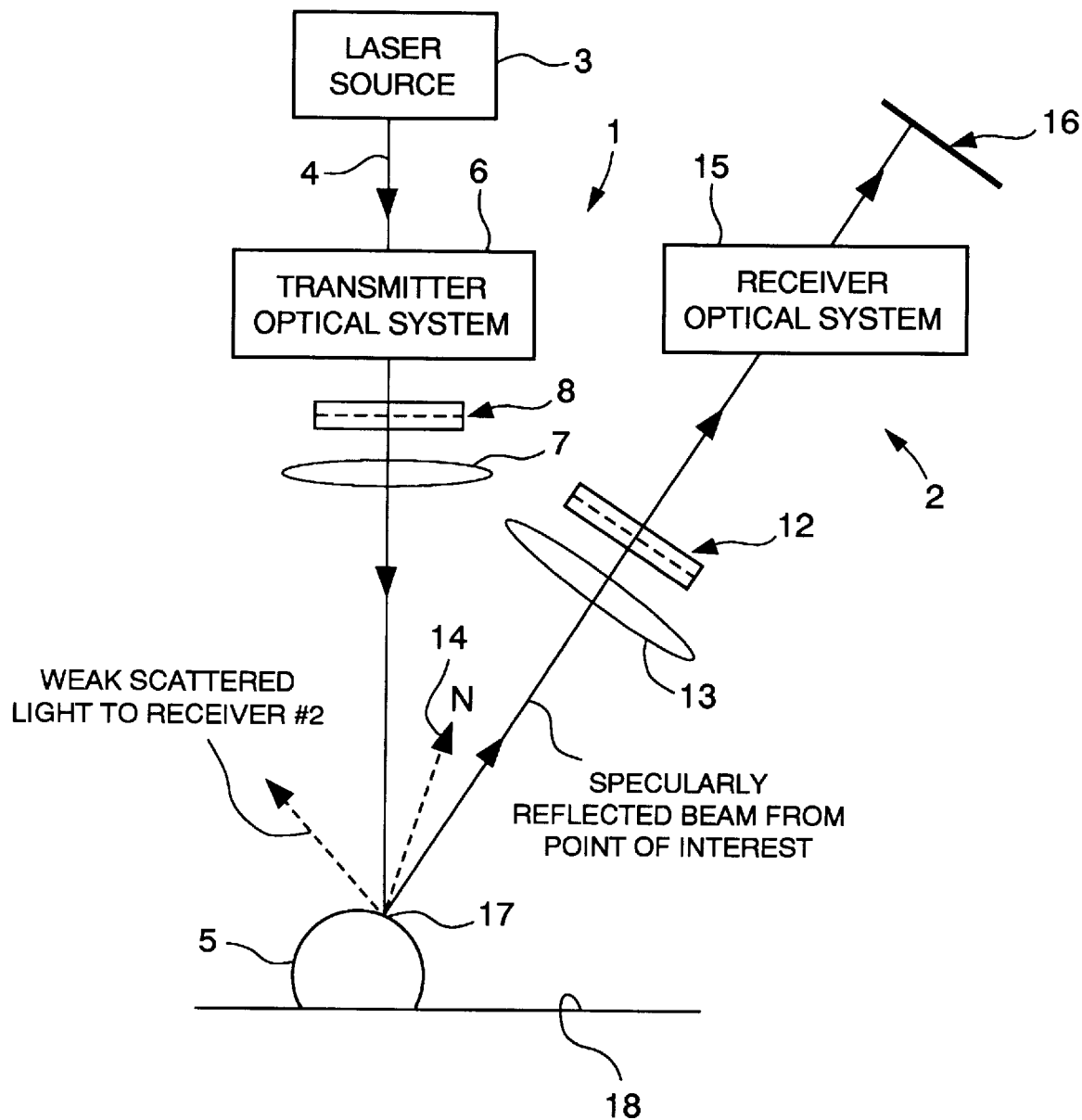
FIG. 3 is a schematic view of a triangulation-based imaging system which illustrates a method for imaging with optical isolators in the transmitter and receiver of the system where a surface normal at the point of interest produces specular reflection at a first receiver.

A first embodiment of the method and system of the present invention includes a transmitter subsystem or transmitter 1 and a receiver subsystem or receiver 2 of a triangulation-based system as illustrated in FIG. 3. Each subsystem 1 or 2 includes an optical isolator, generally indicated at 8 or 12, respectively, or equivalent circular polarizers. The system may be a triangulation-based system, or other imaging system where the receiver 2 and the transmitter 1 are angularly disposed with respect to each other.

The transmitter 1 includes a laser assembly or laser diode source 3 which produces a collimated laser beam 4 which is usually linearly polarized and, after transmission through optical components, is directed toward an object 5 such as a solder ball.

If desired, any scanning methods taught in the art of measurement or laser scanning can be utilized to irradiate a plurality of object sample points without departing from the scope of the invention.

Appropriate combinations of beam expansion or reduction optics are included in a transmitter optical system 6 with a focusing lens 7 to deliver a beam of electromagnetic energy to the object 5. Included, preferably in the collimated beam path, is the optical isolator 8 which converts radiation such as light to a circularly polarized beam. If the beam convergence angle is narrow (i.e. high f/#) the isolator 8 may be placed in the converging path, but polarization efficiency is degraded if the angles are wide. Likewise, it is desirable to restrict the angles of incidence of collimated rays (i.e. scan half angle <10 degrees) whenever the isolator 8 is placed beyond a beam deflector.

If a diffractive scanner (i.e. acousto-optic deflector) is used to scan the object 5, the output polarization may be chosen to be circular (or linear) and the isolator 8 (or circular polarizer) may not be required. However, the primary purpose of the isolator 8 is to prevent back reflected energy (specular or highly polarized "semi-specular" reflection) from entering the laser cavity and should provide a high extinction ratio. Although circular polarizers for the near IR laser diodes often used exist, a preferred method for fabricating the isolator is to use Near IR linear polarizers designated as "Polarcor™" provided by Corning, Inc., which provide extinction ratios of 500:1 or greater; almost a ten-fold improvement over the laser polarization ratio and substantially better than the polarization ratio of the diffractive scanner.

Figure 4:
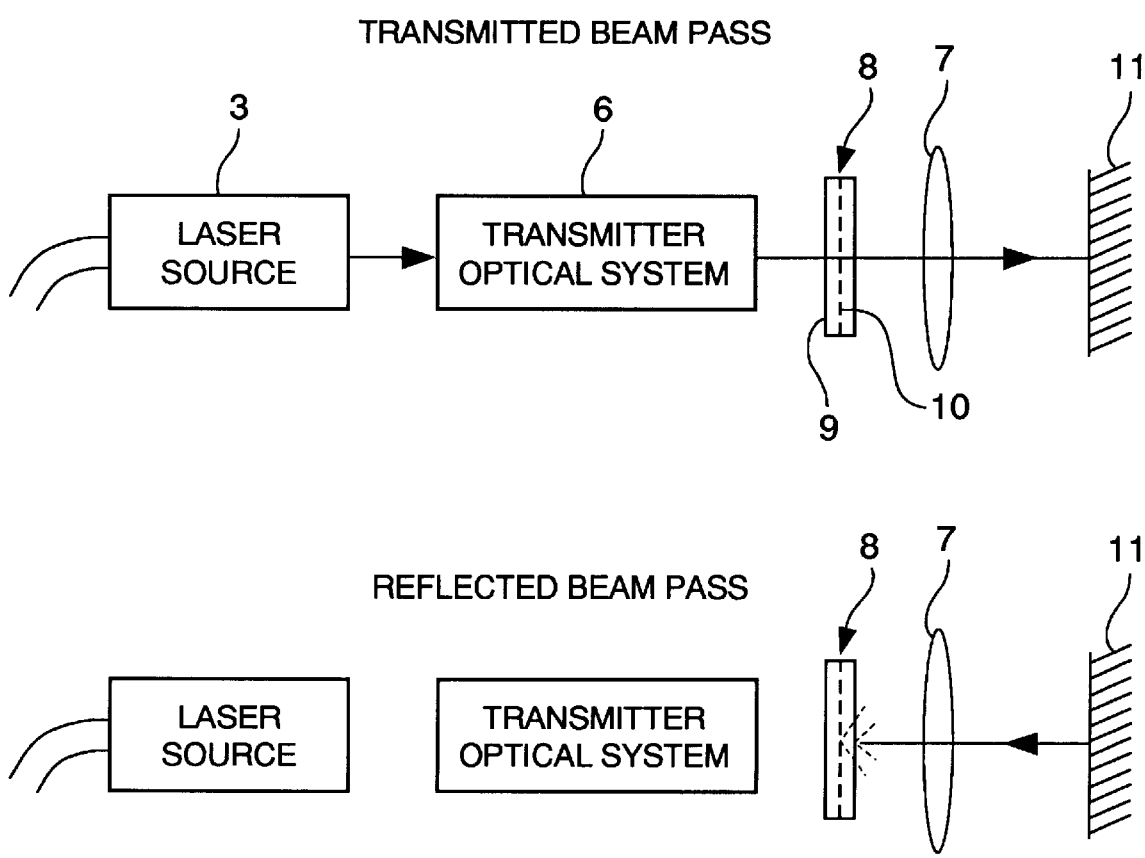
FIG. 4 is a schematic view of a laser-based transmitter system which illustrates the use of a circular polarizer for isolating the system from back reflection.

As shown in FIG. 4, the complete isolator 8 (circular polarizer) is preferably constructed by cementing a quarter wave Mica or Quartz retarder 9 (waveplate) obtained from Karl Lambrect, Inc. to a linear polarizer 10 on appropriate sides so as to construct right or left-handed circular polarizers. Alternatively, a polymer retarder can be used such as the NRQ Series provided by Meadowlark Optics, Inc. A deep optical, anti-reflective coating, such as a V-coat, is recommended to reduce internal reflections or ghost images. Yet another alternative is a commercially available dichroic circular polarizer, provided the performance is sufficient.

The basic operation of the isolator is shown in FIG. 4 where back reflection from a specularly reflective surface such as a mirror 11 is reversed in polarization and hence blocked. If two mirror surfaces are used the original sense is preserved and the beam is transmitted. The metallic surfaces to be imaged are normally rough on a scale compared to the laser wavelength (as opposed to polished); so the reflected beam will actually be elliptically polarized and the effective isolator extinction is reduced, but the energy in the back reflected beam is both scattered outside the acceptance angle of the transmitter and retro-reflected.

The circularly polarized beam shown in FIG. 3 (preferably scanned with an acousto-optic deflector and an optical isolator) is incident on the object 5 and, after specular reflection from a metallic surface thereof, is substantially reversed in polarization. The optical isolator 12 in the receiver 2 is shown adjacent to a telecentric receiver lens 13 of the receiver 2 for clarity but may be disposed in other locations in the path, preferably where beam angular variations are minimal (a recommended location being a telecentric stop to minimize the required clear aperture and cost). In any case, the extinction ratio, which varies somewhat with angle of incidence, is the key isolator parameter.

The isolators 8 and 12 can be identical in construction except for retarder axes are offset by 90 degrees to produce opposite sense circular polarized beams. If RCP (Right Circular Polarized) radiation is incident on the object 5, the reflected beam will be LCP (Left Circularly Polarized). For instance, if a normal outward angle 14 of the illuminated surface element in FIG. 3 is angled away from the transmitter 1 and bisects the angle between the transmitter 1 and receiver 2 then a specular reflected beam, reversed in polarization, is collected by the receiver lens 13 and transmitted through a receiver optical system 15 to an image sensor or detector 16 (rather than to the laser diode source 3). The receiver isolator 12 is oriented opposite the transmitter isolator 8 in that the beam first passes through the retarder before passing through the linear polarizer which allows the specular reflection to pass.

A second, substantially identical, symmetrically placed receiver (not shown in FIG. 3) collects a much weaker diffuse and approximately random polarized component which is partially transmitted (50% nominal) by an isolator of the second receiver through its optical system to its detector. With the angled facet the feedback light to the laser diode source 3 is now negligible.

In certain cases it may be desirable to utilize elliptical polarization analysis in the receiver, recognizing that circular and linear polarization are special cases of elliptical polarization. An elliptical polarizer may be constructed using a suitable compensation for the retarder, adjustable if so desired. Likewise, for imaging certain materials, particularly metallic surfaces, a pair of elliptical polarizers, one each in the transmitter and the receiver, may be preferred based upon analysis of the material properties. For example, typical conductors used in the microelectronics industry are copper, tin lead, and gold. The optical constants of metals varies greatly but useful characterization has been achieved with ellipsometry (see, for example, Jenkins, White, "Fundamentals of Optics," Fourth Edition, 1976, pages 534–540). Such a priori knowledge of the material characteristics in conjuncton with a geometric model of the part may be used to optimize the receiver configuration, providing "matched polarization" filtering characteristics with a single image. Furthermore, combinations of geometric constraints, material characteristics (dielectric or metal) for primary reflection and secondary reflection may be exploited.

Both detector signals can be used if the dynamic range of the detector and signal processing electronics is sufficiently wide. However, often the specular component is strongly asymmetric. Further information regarding these system elements and solutions to the dynamic range and spot asymmetry problems can be found in U.S. Pat. Nos. 4,796, 997 and 5,024,529, and the above-noted copending related applications. In each case, the signals received by each detector and processed to compute depth are based upon an estimate obtained from each of the wide dynamic range signal processing channels.

Figure 5:
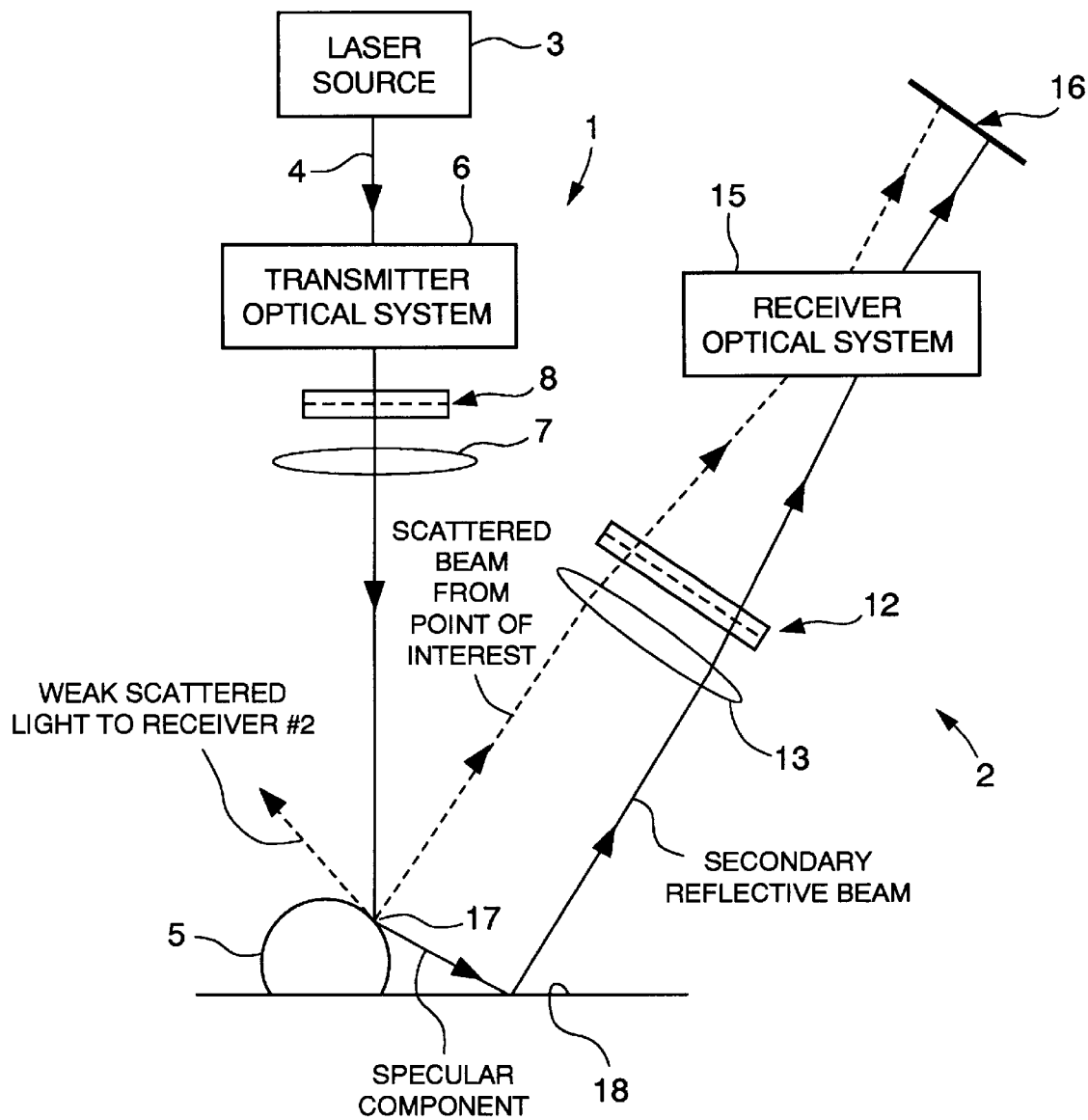
FIG. 5 is a schematic view of a triangulation-based imaging system which illustrates a method for imaging with optical isolators in the transmitter and receiver of the system, where a surface normal at the point of interest produces specular reflection onto the background which is again reflected to a first receiver of the system.

A key case to consider for the present invention is when the specular reflected beam is neither directed to the receiver 2 nor retro-reflected to the transmitter 1. Referring to FIG. 5, there is illustrated an imaging system similar to the imaging system of FIG. 3 (and consequently have the same reference numerals) wherein it is shown that in many cases the energy is specularly reflected or scattered (often over a narrow angle) from the point of interest 17 to a neighboring surface 18 which has a sufficiently high reflection coefficient to produce detectable energy levels at the detectors (only one of which is shown at 16).

Figure 1:
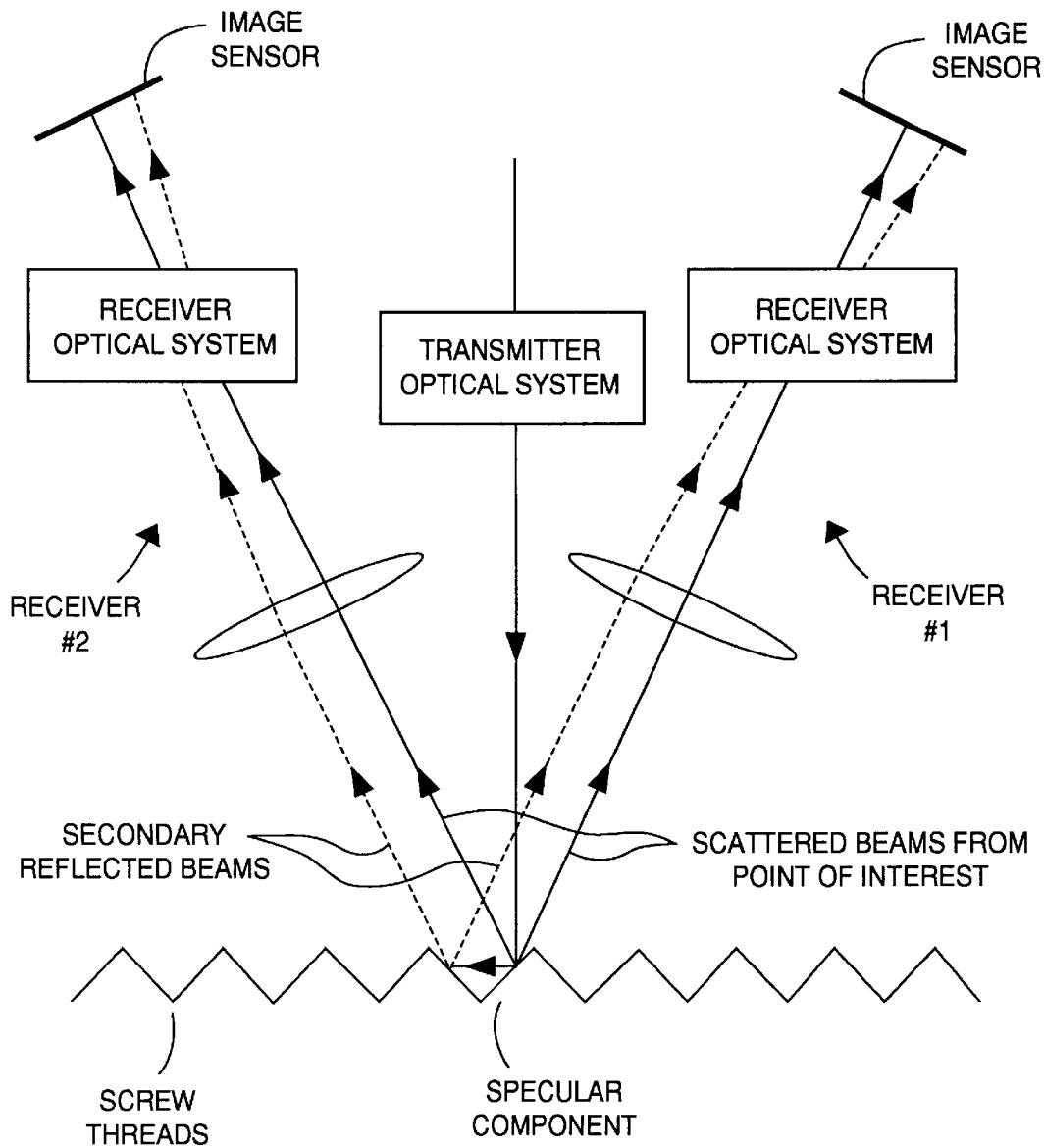
FIG. 1 is a schematic view of a prior art imaging system which shows the problem of thread gauging where readings at both sensors are in error as a result of partial occlusion and multiple reflections.
Figure 2:
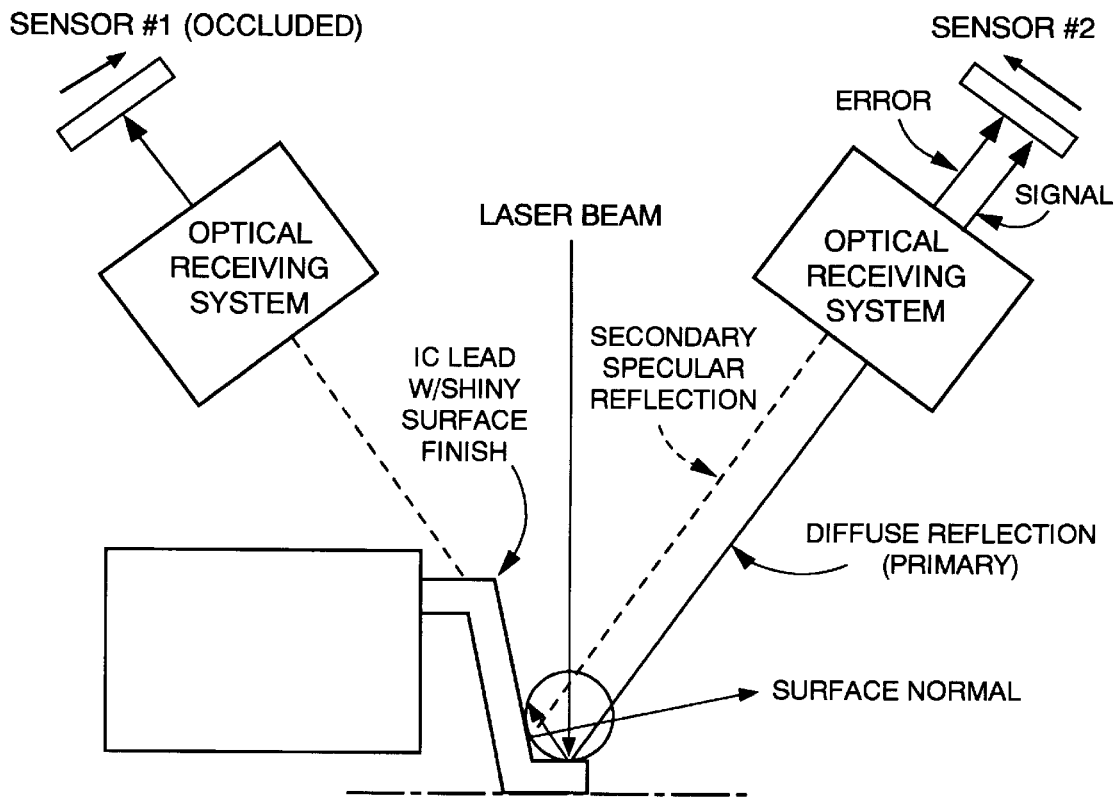
FIG. 2 is a schematic view of another prior art system which illustrates the problem of inter-reflections (and occlusion) as observed when imaging the leads of an integrated circuit chip providing a scenario where both readings are again potentially in error.

As shown in FIGS. 1 and 2, secondary reflection can render the imaging system useless for inspection of metallic IC leads and more complex surfaces like screw threads. As shown in FIG. 2, the first sensor suffers from the fundamental limitation of partial or complete occlusion, and the second sensor receives energy from the point of interest but an error from a secondary (specular) component is present. It is not uncommon for the secondary reflection reading to easily exceed the signal readings and produce false data, particularly if the secondary reflection has a strong specular component as shown in FIGS. 1 and 2.

Those skilled in the art will quickly recognize that an arbitrary number of cases can be formed by varying the shape (convex and concave) of the object surfaces and the surface (specular and diffuse) reflection coefficients, and hence affect the resulting "purity" of the polarization. However, although not obvious from ray trace analysis, the "microfacet model" referred to by the above-noted reference Clark et al., predicts that secondary reflection, particularly from metal-metal surface reflections, will be sufficiently attenuated for polarization discrimination. The sense of the secondary reflection is substantially identical to that of the incident beam reflection and hence attenuated by the isolator 12 thereby producing a negligible error contribution from the detector 16, provided that the isolator extinction ratio is high. It is important to note that specular secondary reflection components may exceed corresponding diffuse components representing the point of interest by several orders of magnitude. Conversely, diffuse secondary reflection components may be several decades weaker than the desired signal.

It is further recognized that with regard to multiple reflections in which degree of polarization is at least partially preserved, a large number of secondary illumination and surface angles may be encountered when only one point of interest is illuminated, and that each component reflection of that large number may have a unique eccentricity of elliptical polarization. Since the secondary reflections originate from a spatially varying assembly of object locations, a priori knowledge of the object geometry and material content may be used to construct a model from which the reflection behavior for a given area of interest may be predicted. Using this model, the preferred embodiment of the present invention may be optimized as follows: a fixed device with a varying degree of retardance over the field or over varying angles of incidence, depending on the location placed in the receiver, may be employed (in conjunction with a linear polarizer of optimized orientation) in place of the optical isolator 12 to maximize secondary reflection suppression for a particular object fitting the model.

It is worthwhile to note that if the receiver isolator 12 is of incorrect handedness (i.e, the handedness is identical to the handedness of the transmitter isolator 8), the resulting image will provide a very poor representation of the object geometry, with a high contrast error image produced by false data. Hence useful (random or strongly polarized) energy is rejected and large errors are introduced by accepted secondary reflected beams.

Although the above embodiment was demonstrated with fixed orientations for each of the isolators 8 and 12, it will be apparent to those skilled in the art that "dynamic" methods analogous to those described in the above-noted references can be adapted for further polarization discrimination. A natural extension is optimization of the method for use with dielectric surfaces, or surfaces in which primary components are diffuse rather than specular. However, the results here indicate that large improvements were found with a static case. Improvements in device quality and technology are needed to fully realize possible improvements with dynamic LCD based polarization cameras as the extinction ratios are marginal at best. A typical specification is 16:1, but 1000:1 has been demonstrated with Ferroelectric Devices, as produced by Display-Tech, Boulder Colo.

It is known in the art that rotating devices can be used to vary the angles of the analyzers (receiver section), but this requires multiple moving parts in the imaging head (which includes the transmitter and receiver) and is often undesirable. In any case, the circular polarization based method provides the additional advantage of isolating the laser source 3 from back reflections and further reducing instrument-based stray light and ghost images.

Reducing Instrument Back Reflection

In FIGS. 3 and 5 depth information is derived using the triangulation principle. The surface of the object 5 shown on a specular reflecting dielectric film background surface 18, has a strong component of specular reflection (at the point of interest 17) which is directed toward the receiver 2, while a relatively weak diffuse component is received by a second receiver (not shown) placed symmetric and opposite the transmitter axis. The specular component is often strongly asymmetric which results in some position estimation error. More important, the specular component is very strong (directly proportional to surface reflection coefficient) while the diffuse component may be several orders of magnitude weaker (inversely proportional to product of the squares of the receiver f/# and standoff).

Figure 6:
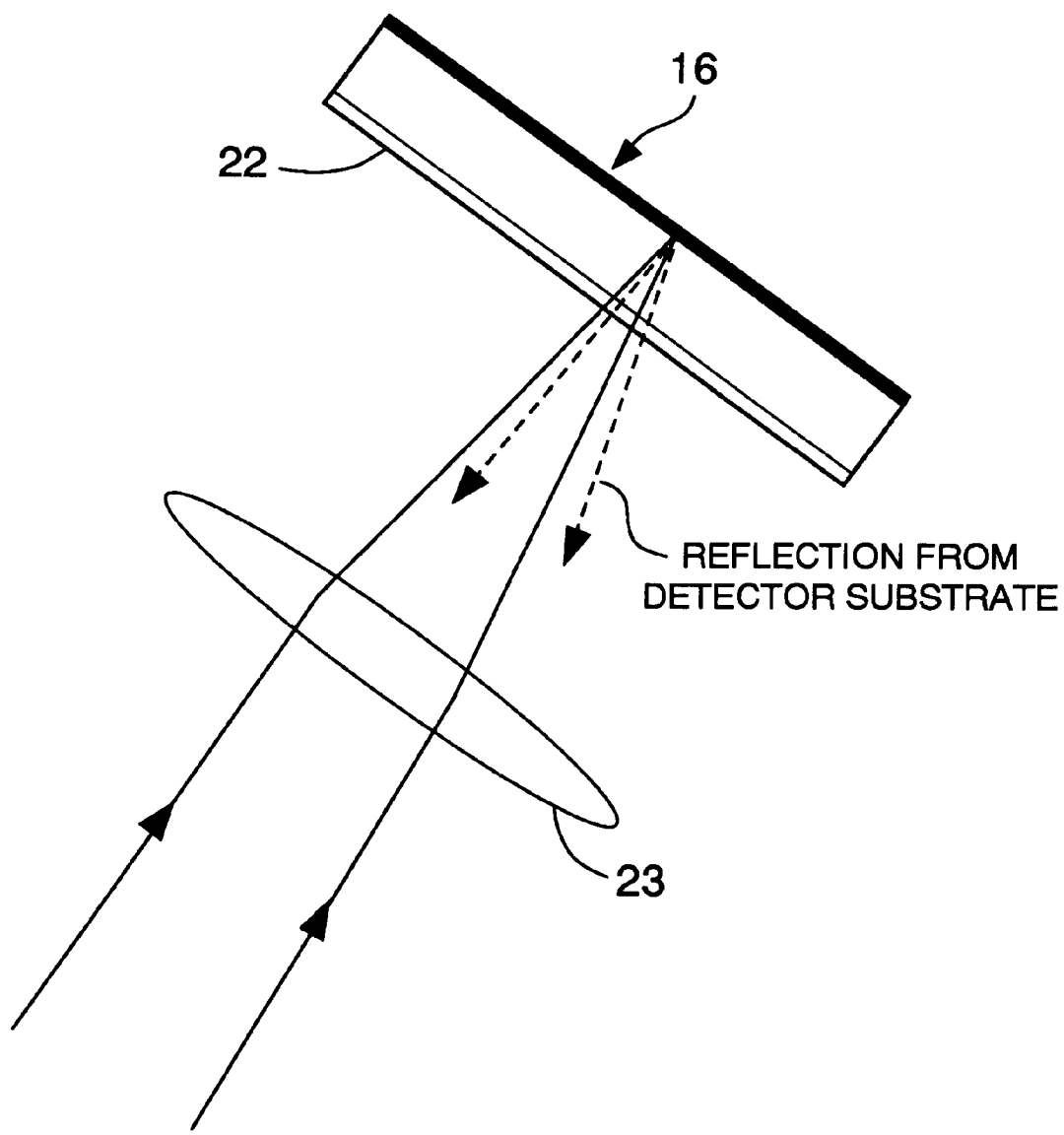
FIG. 6 is a schematic view of a silicon photodiode which illustrates a problem of back reflection observed from the photodiode despite the use of a anti-reflection coated window thereon.

As shown in FIG. 6, the detector 16, which may be a silicon detector, only converts a fraction of incident electromagnetic energy (passing through its window 22 from an imaging lens 23) into current and, even at more sensitive near IR wavelengths, about 30% of the energy is transmitted through the silicon to the mirror-like back surface metallization (defocused at this point) and retro-reflected with a second pass through the silicon producing a net 10% back reflection to the scene.

Figure 7A:
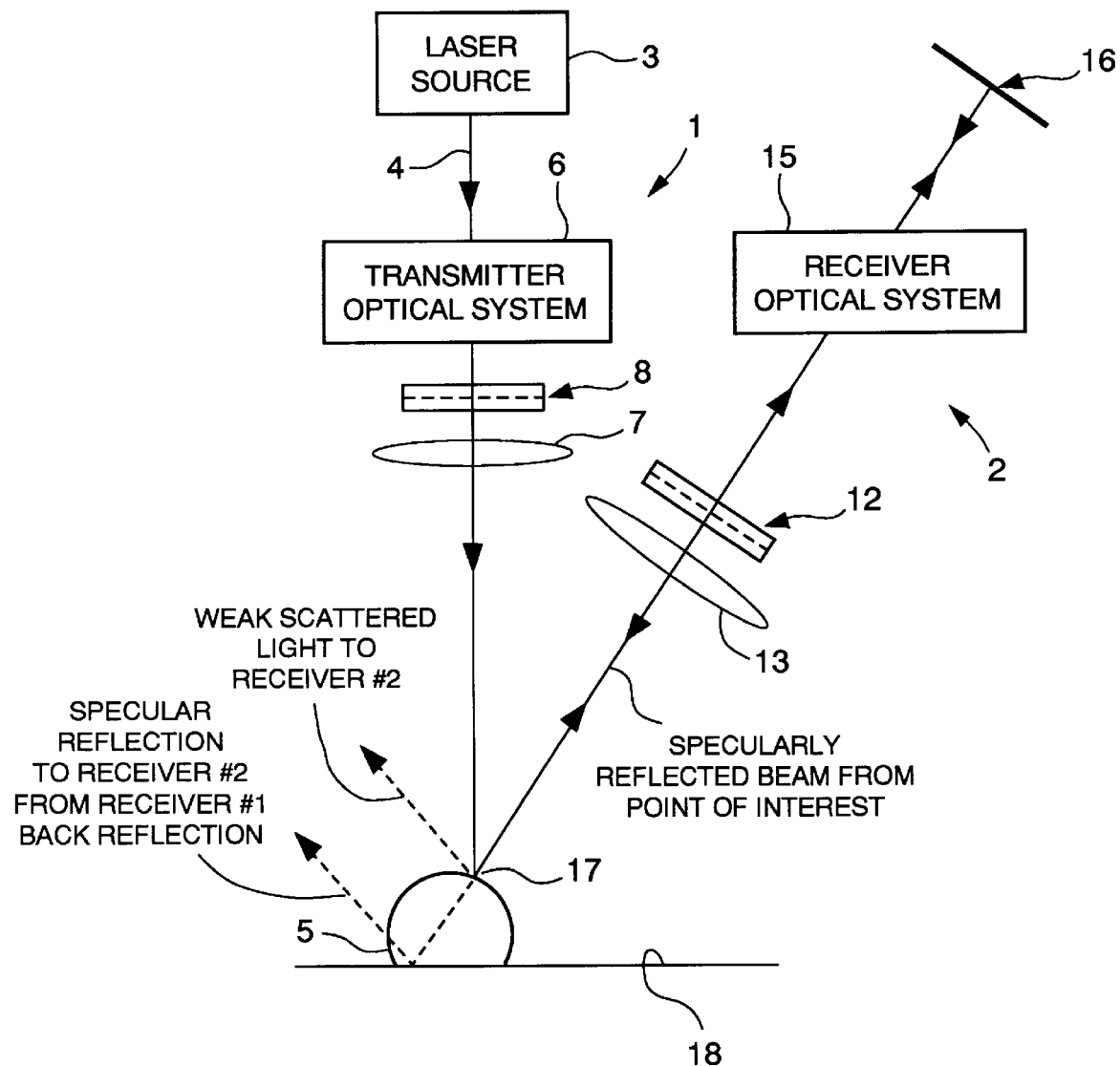
FIGS. 7a and 7b are schematic views of a dual detector system which illustrates corruption of a measurement in the system caused by 1) back reflection from the detector surface, 2) specular reflection from the scene, 3) with specular reflection received by a second detector.
Figure 7B:
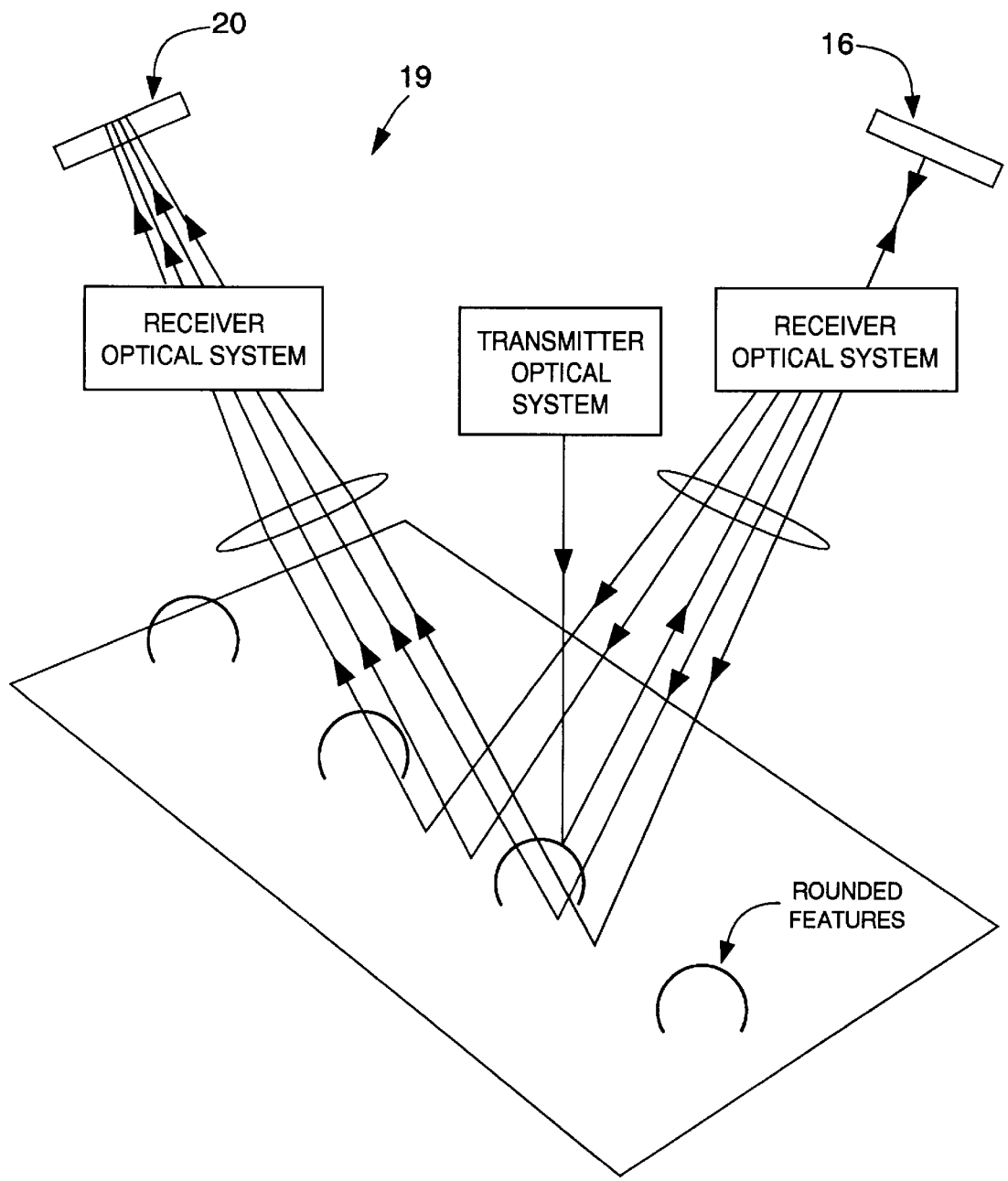

As shown in FIG. 7b, a ghost image is formed by a combination of back reflection and additional specular reflection from the mirror-like substrate background 18 into a second receiver 19 introducing a large bias in the signal, where the error will easily exceed the weaker signal from the object (i.e. solder ball) surface with a surface normal directed away from the second receiver 19.

For example, assume the solder ball surface has a 10% specular reflection component, optical element reflection losses of each receiver are negligible, 30% is transmitted by the detector 16 on each pass of the beam, and the substrate film is an 80% specular reflector. The fraction of laser power represents a huge error contribution from a detector 20 of the receiver 19. If a laser with peak power of 40 mw like the Sharp LT-015MD or Spectra Diode Labs 5700 Series is used, then up to 960 uw of stray energy is available for a ghost image. The diffuse component of interest produces signals often corresponding to about 30–50 $\mu$W, resulting in unusable optical signal-to-noise ratio. Although not all the stray energy may be delivered to the detector 20, it is clear that the potential for degradation is great.

It is well known in the triangulation and off-axis imaging art that the Scheimpflug imaging condition can be employed which defines the detector tilt to maintain focus over a depth range. However, it can be shown that this condition may not always be a practical choice for imaging at narrow triangulation angles (desirable for shadow reduction) and high magnification (to produce fine depth sensitivity as required for microelectronics). Often the detector is oriented nearly orthogonal to the line of sight. This, however, provides direct back reflection to the object.

Figure 8:
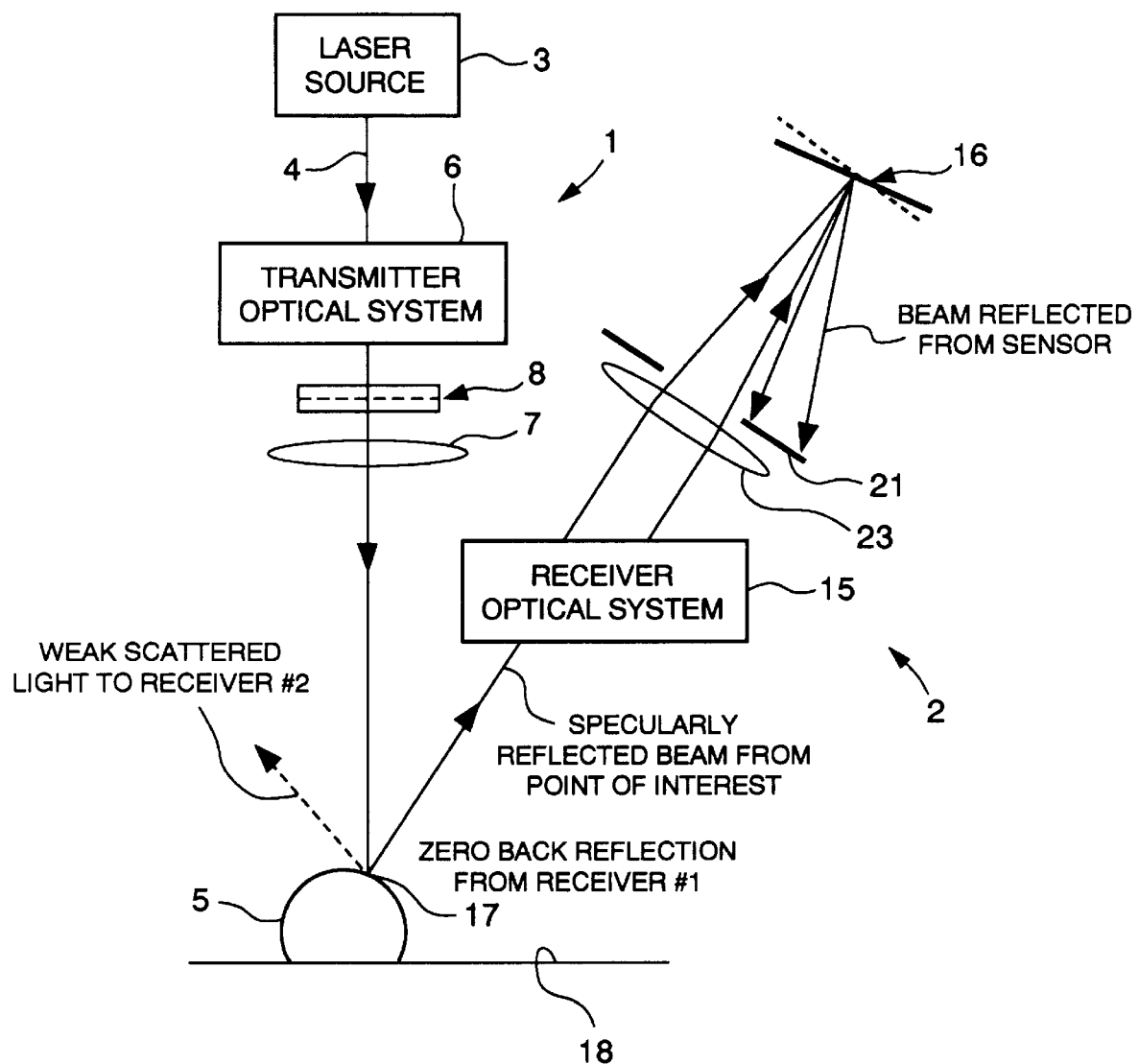
FIG. 8 is a schematic view of an imaging system which illustrates the effect of slight detector tilt, with observed reduction in error exceeding 100X.
Figure 9:
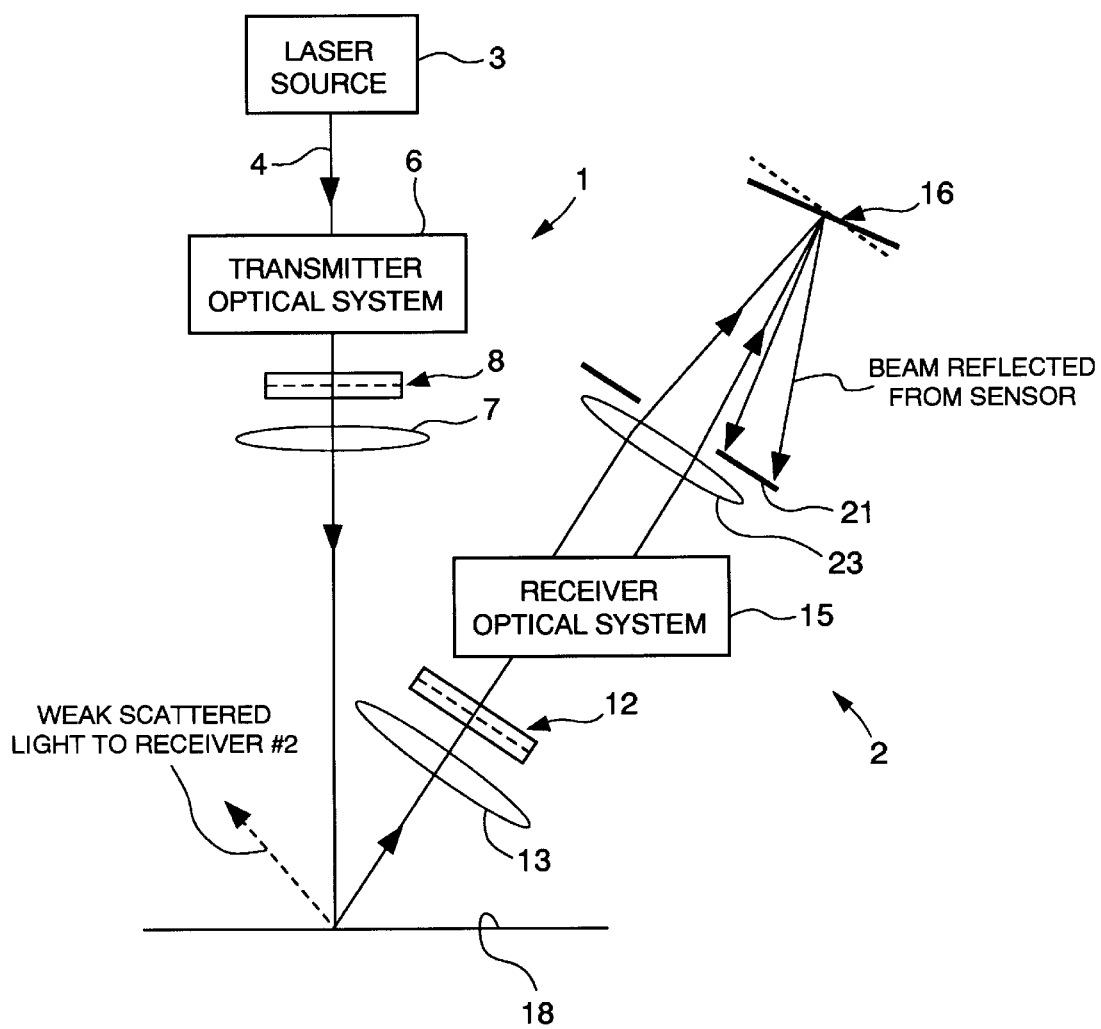
FIG. 9 is a schematic view of an imaging system including an isolator pair and tilted detector.

In a preferred embodiment of FIG. 8, the detector 16 (as well as the detector 20 in a two receiver system) is oriented (from its dotted line position) at a slight angle (i.e. indicated by a solid line) which is large enough for the back reflected beam to impinge upon a scattering and absorbing surface such as a back surface of a lens mount or baffle 21. The higher the optical magnification of the receiver 2, the less the angular tilt required to "shunt" the beam.

The preferred embodiment is successful in practice for measurement of ball grid arrays (BGAs) on a specular reflective background; an improvement of at least 2 decades in depth accuracy is typically realized. The specular back-reflected light would pose less of a problem if only a single receiver is used or if the background produced weak, scattered light. However, such a single receiver system is plagued by other shadow and secondary reflection errors. Back reflections from other optical elements such as the isolator 12, the lens 13, and the optical system 15 within each of the receivers 2 and 19 are negligible because of the action of their corresponding isolators (on odd numbered reflections) and the use of deep optical coatings (0.2% per surface reflection typical). The problem of imaging specular targets on specular backgrounds is very common in the industry, demonstrating the importance of this optical error reduction method.

Other Embodiments

An additional embodiment is formed by a combination of the two above-described methods. Furthermore, the general teachings of U.S. Pat. No. 5,024,529 and other disclosed polarization and filtering techniques can be combined with the teachings herein to further improve performance.

The use of the invention is illustrated herein primarily with triangulation based imaging systems. It is to be understood, however, that the principles described here are useful in many instruments, including laser radar, confocal microscopy, and systems used to quantify surface color, reflections, or other characteristics.

While the best mode for carrying out the invention has been described in detail, those familiar with the art to which this invention relates will recognize various alternative designs and embodiments for practicing the invention as defined by the following claims.

What is claimed is:

1. The system of suppressing unwanted reflections in 3D imaging system including a source of electromagnetic energy, optical elements for directing a beam of the electromagnetic energy to an object having a point of interest, means including an optical isolator for polarizing the beam of electromagnetic energy in a first rotational sense, the polarized beam of electromagnetic energy being incident upon the point of interest of the object, the object being capable of reflecting the polarized beam of electromagnetic energy to obtain reflected electromagnetic energy, and a receiver having a detector for collecting the reflected electromagnetic energy, wherein the improvement comprises:

means including a polarizer for filtering the reflected electromagnetic energy wherein reflected electromagnetic energy polarized in the first rotational sense is attenuated and reflected electromagnetic energy polarized in a second rotational sense opposite to the first rotational sense is passed and wherein secondary and other even numbered reflections from locations other than the point of interest on the object are suppressed and wherein the receiver is a triangulation-based 3D receiver and wherein the reflected electromagnetic energy is polarized along major and minor axes and wherein the ratio of the minor axis to the major axis is substantially equal to 1.

2. The system as claimed in claim 1 wherein the triangulation-based 3-D receiver has a triangulation angle substantially 20° or less.

* * * * *